United States Patent
Schonemann et al.

(10) Patent No.: US 7,329,789 B1
(45) Date of Patent: Feb. 12, 2008

(54) METHOD FOR EXTRACTION AND CONCENTRATION OF CAROTENOIDS USING SUPERCRITICAL FLUIDS

(75) Inventors: Hans Schonemann, Newburyport, MA (US); Anthony Gudinas, Atkinson, NH (US); Kara Williams, Saugus, MA (US); Paula Wetmore, Chelmsford, MA (US); Val Krukonis, Lexington, MA (US)

(73) Assignee: Phasex Corporation, Lawrence, MA (US)

( * ) Notice: Subject to any disclaimer, the term of this patent is extended or adjusted under 35 U.S.C. 154(b) by 753 days.

(21) Appl. No.: 10/281,335

(22) Filed: Oct. 25, 2002

Related U.S. Application Data

(60) Provisional application No. 60/343,577, filed on Oct. 25, 2001.

(51) Int. Cl.
*C07C 13/00* (2006.01)
*C07C 403/24* (2006.01)
*B01D 11/04* (2006.01)

(52) U.S. Cl. .................... 585/351; 585/1; 585/20; 210/634; 424/425

(58) Field of Classification Search ............ 585/1, 585/20, 351; 210/634; 424/425
See application file for complete search history.

(56) References Cited

U.S. PATENT DOCUMENTS

| | | | |
|---|---|---|---|
| 4,384,085 A | 5/1983 | Smith | |
| 4,439,629 A | 3/1984 | Rüegg | |
| 5,789,647 A | 8/1998 | Heidlas et al. | |
| 5,932,101 A * | 8/1999 | Kanel et al. | 210/634 |
| 6,299,906 B1 | 10/2001 | Bausch et al. | |
| 2001/0031282 A1 * | 10/2001 | Peter et al. | 424/489 |
| 2002/0086059 A1 * | 7/2002 | Bausch et al. | 424/489 |

* cited by examiner

*Primary Examiner*—Elizabeth D. Wood
(74) *Attorney, Agent, or Firm*—Nutter, McClennen & Fish LLP

(57) ABSTRACT

Carotenoids are extracted and/or enriched from a mixture containing such compounds. The extraction/enrichment process involves the use of liquefied or supercritical solvents to extract lipids and carotenoids from carotenoid-containing substrates. The extraction process can also be performed in two steps in which lipids and carotenoids are first removed from a carotenoid-containing substrate with a liquefied or supercritical solvent, and subsequently a liquefied or supercritical gas is used to separate the lipids from the carotenoids. The two step process can be reversed to first extract lipids with the liquefied or supercritical gas, and subsequently use the solvent to extract the carotenoids. The process is also applicable to yield an organic solvent-free product from a carotenoid-containing source that was first extracted using an organic solvent.

7 Claims, 2 Drawing Sheets

METHOD FOR EXTRACTION AND CONCENTRATION OF CAROTENOIDS USING SUPERCRITICAL FLUIDS

REFERENCE TO RELATED APPLICATION

This application claims priority from U.S. Provisional Patent Application Ser. No. 60/343,577, filed on Oct. 25, 2001, entitled "Method for Extraction and Concentration of Carotenoids Using Supercritical Fluids," which is expressly incorporated by reference herein.

FIELD OF THE INVENTION

The present invention relates to the extraction and/or enrichment of carotenoids from a mixture containing such compounds. More particularly, methods for extracting carotenoids from botanical and biological substrates, such as algae and vegetable substrates, using liquefied and/or supercritical gases are disclosed.

BACKGROUND OF THE INVENTION

Carotenoids are natural pigments that are responsible for many of the yellow, orange, and red colors seen in living organisms. Carotenoids are widely distributed in nature and perform a number of important biological functions, including protecting organisms from photo-oxidative damage. In the human body carotenoids provide powerful antioxidant action. Antioxidants help form the body's defense against free radicals, which develop as a result of normal metabolism as well as from exposure to pollution and other environmental hazards.

Carotenoids also serve as light-harvesting pigments in photosynthesis. Carotenoids, such as lutein, zeaxanthin, astaxanthin, β-carotene and lycopene, and their esters are valuable as feed additives for improving the color of chickens and bred fishes (such as salmon and trout), and many carotenoids are increasingly being used as food additives and dietary supplements for human consumption.

Extracted and/or enriched carotenoids can be used as nutraceuticals, dietary supplements, or pharmaceuticals. The nutraceuticals industry employs liquid organic solvents to extract carotenoids and lipids from natural substrates. Hexane and acetone have traditionally been used for many extractions, especially for carotenoids like astaxanthin. However, because of increasing scrutiny and concerns about safety and toxicity, both solvents are losing favor within the nutraceuticals industry as extractants. Furthermore, it is anticipated that the use of lipid organic solvents for natural products extraction may be strictly regulated in the future, hence there is need for a more acceptable alternative. In any event, after such extraction with organic solvents, distillation is required to remove the organic solvent(s) from the extracted carotenoid fractions. The high temperature required for distilling the final solvent remnants can degrade the sensitive extract. Hexane and acetone are being replaced, when possible, with ethanol or other less toxic liquids; however, even the use of ethanol can harm the sensitive extract during the distillation step when the solvent must be boiled off.

Supercritical fluids and liquefied gases, have been used as gaseous solvents for extracting lipids, essential oils, sterols, and many other classes of compounds from botanical or marine substrates. Carbon dioxide has been used predominantly, but it is not always capable of extracting relatively polar or high molecular weight compounds (such as astaxanthin). Some of the light hydrocarbons, e.g., propane and butane, have been used, but sometimes with only limited success. For example, U.S. Pat. No. 5,789,647 to Heidlas et al., discloses the use of liquefied gases, e.g., propane and butane, to extract carotenoids from various substrates (e.g., vegetable, fungal and fermentation derived substrates) when carbon dioxide does not achieve satisfactory yields. Use of these liquefied gases, was found unsatisfactory in achieving high yields of carotenoids. Despite the addition of organic solvents (called entrainers when used with supercritical or liquefied gases) such as ethanol, acetone, and ethyl acetate to the gas, yields of carotenoids were, occasionally, still low. Reported yields were as low as 60%, in some cases. Besides the low yields encountered, residual organic solvents must still be removed from the extract. Whereas small quantities of ethanol might be acceptable in the final product, traces of entrainers such as acetone and ethyl acetate would not be acceptable in products intended for human consumption or use.

There is a need for an economic and efficient method to extract carotenoids from mixtures that eliminates the use of liquid organic solvents and provides acceptable product yields.

SUMMARY OF THE INVENTION

Exemplary embodiments of the present invention provide methods for extracting various carotenoids from mixtures. Mixtures may include algae, yeast cells, plant or vegetable substrates, and carotenoid-containing extracts obtained from these substrates. An exemplary algae substrate containing carotenoids is *Haematococcus pluvialis*; yeast, and suitable plant and vegetable substrates include, among others, tomatoes, corn, marigold petals, and spinach. One having ordinary skill in the art will recognize applicable biological and botanical substrates and the carotenoids that can be derived therefrom.

An embodiment of the extraction method includes the use of liquefied or supercritical solvent (e.g., dimethyl ether) to extract lipids and carotenoids from substrates including algae, yeast cells, or vegetable substrates. By way of example, astaxanthin is extracted from *Haematococcus pluvialis* cells, which are prepared for extraction by known processes that include harvesting, drying, and cracking the cell walls.

In another embodiment, an extraction solvent such as dimethyl ether is used in a two step process. First, the dimethyl ether extracts lipids and carotenoids from a substrate. Subsequently, another liquefied or supercritical gas, e.g., carbon dioxide, is used at a pressure in the range of about 1500 psi to 5000 psi (and more preferably at 1500 psi to 3000 psi) and at a temperature in the range of about 35° C. to 80° C. to separate lipids from the carotenoid-containing extract, thereby concentrating the resulting carotenoids.

In a further embodiment, a liquefied or supercritical gas, e.g., carbon dioxide, is first used at a pressure in the range of about 1500 psi to 5000 psi (and more preferably at 1500 psi to 3000 psi) and at a temperature in the range of about 35° C. to 80° C. to extract lipids from a substrate and the concentration of astaxanthin in the product can be manipulated or tailored depending upon the amount of lipid that is removed. In a second step, a solvent such as dimethyl ether is used to extract carotenoids (e.g., astaxanthin, zeaxanthin, etc.) from the same substrate to produce a concentrated carotenoid fraction.

In the event that a liquid organic solvent such as acetone or hexane is first used to extract lipids and carotenoids from a carotenoid-containing source, an organic solvent-free product can be obtained in still another embodiment by extracting the solvent-containing extract with liquefied or supercritical carbon dioxide under operating conditions that will separate essentially only the solvent or that will separate essentially only solvent plus lipids, thus concentrating astaxanthin. By way of example, $CO_2$ can be used in such an extraction process, in either a liquefied or supercritical state, at a pressure and temperature over a range of about 800 to 3000 psi and about 20° C. to 100° C.

DETAILED DESCRIPTION OF THE INVENTION

Generally, ethers (and particularly liquid ethers such as ethyl ether) are good solvents for dissolving many organic materials. Ethers dissolve a wide range of polar and nonpolar substances and are also good solvents for many hydrogen-bonded substances (e.g., water.) Hydrogen-bonded substances need more solvation energy to break the hydrogen bonds that hold such molecules together and ethers can act as hydrogen bond acceptors, forming hydrogen bonds with hydrogen-bonding solutes. Ethers also have relatively low boiling points and are relatively easily evaporated from products. For example, diethyl ether is used in the pharmaceutical industry as an extract solvent, however the potential build up of harmful peroxides limits its use. The particularly low boiling point of dimethyl ether, −25° C., is especially advantageous as it is a gas at atmospheric pressure and room temperature.

Therefore, products extracted with dimethyl ether are produced substantially solvent free. However, dimethyl ether is an example of an ether not generally employed as an industrial solvent since it must be compressed to a liquid state or to a supercritical state to become a solvent.

As used herein, the term "supercritical fluid" denotes a gas or liquid that is above both its critical temperature and critical pressure. This term includes both single fluids and fluid mixtures. The term "liquefied" denotes a gas that is below its critical temperature and is compressed to a point above its vapor pressure, which may or may not be above its critical pressure.

The present invention provides methods for extracting various carotenoids from mixtures. In one embodiment, the mixture, a carotenoid-containing substrate (e.g., *Haematococcus pluvialis*), is exposed to a liquefied or supercritical solvent such as dimethyl ether. This process results in the extraction of the carotenoid astaxanthin at a yield of about 98% from the substrate whose astaxanthin-containing cells have been "cracked", i.e., ruptured. The invention is applicable to the extraction of a variety of additional carotenoids, including zeaxanthin, lycopene, lutein, and esters of the carotenoids, and other carotenoids known to those having ordinary skill in the art.

Unlike prior art techniques that use liquefied or supercritical fluids to extract carotenoids from substrates, dimethyl ether, according to the present invention, has been found to be capable of solubilizing and extracting essentially all of the carotenoids contained in the carotenoid-containing mixture.

Figure 1:
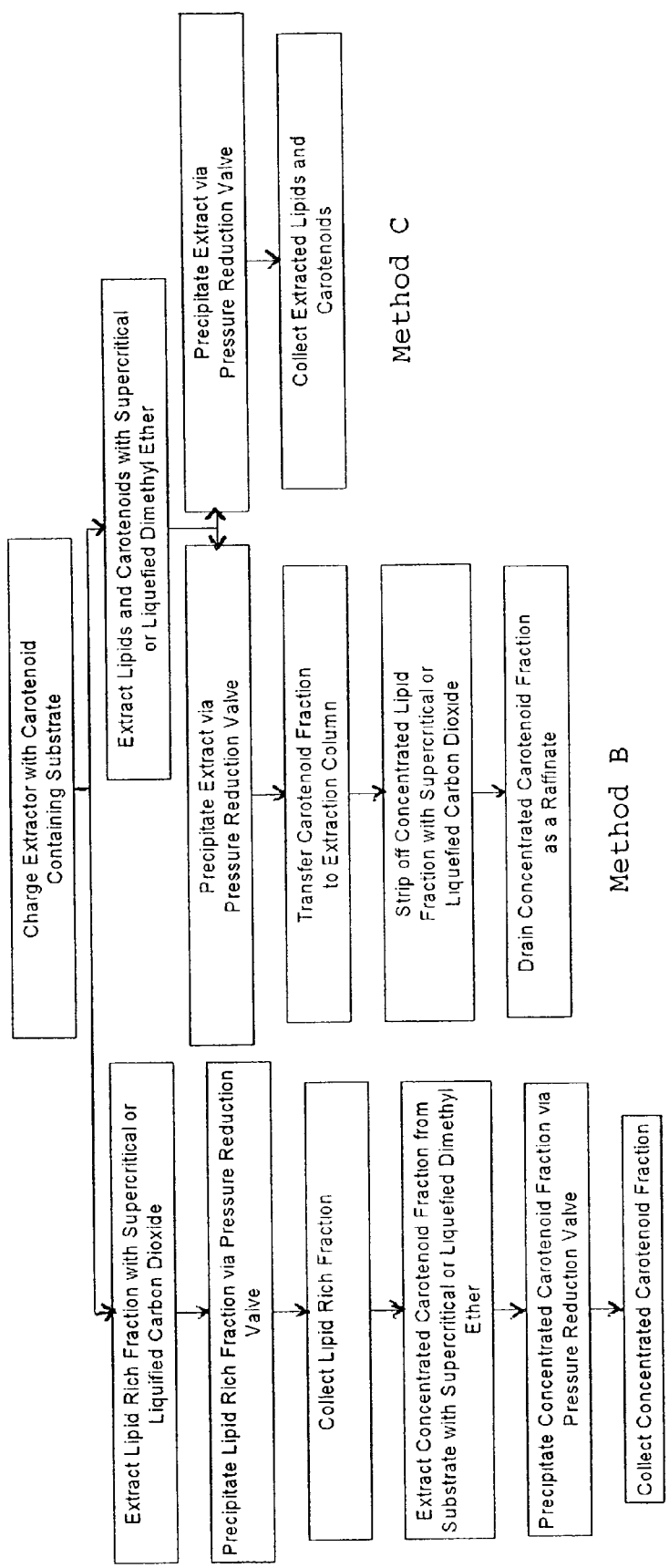
FIG. 1 is a flow chart illustrating various extraction techniques according to the present invention.

FIG. 1 illustrates three processes for extracting carotenoids from carotenoid-containing substrates.

According to the present invention, carotenoids are extracted from a carotenoid-containing mixture by exposure to a solvent such as supercritical or liquefied dimethyl ether. As a general methodology for extraction of carotenoids, a known quantity of a carotenoid-containing mixture is charged to an extraction vessel. The extraction vessel is sealed, brought to process temperature and pressure, and an extractant gas is passed through the vessel.

Subsequently, supercritical or liquefied dimethyl ether is used to extract the carotenoid fraction as a concentrated extract. The gas and the dissolved extract then exit the extraction vessel through a valve that reduces the vessel pressure to a level that results in the precipitation of the dissolved extract. Alternatively, a temperature reduction, or a combination of pressure and temperature changes, may be used to separate the dissolved extract from the gas. The gas and extract are then directed to a collection chamber which retains the precipitated extract while allowing the gas to exit the collection chamber. If desired, it is possible to use a dry test meter to measure the total volume of the gas exiting the collection chamber. Further, in a production scale process, the low pressure gas leaving the collection chamber may be compressed and recycled to the extraction vessel. One having ordinary skill in the art will recognize the process variations that can be applied and manipulated to achieve the desired concentration of the extract.

Carotenoid-containing mixtures include, but are not limited to algae, algae-derived material, yeast cells, plant or vegetable substrates, and carotenoid-containing extracts. A variety of carotenoid-containing algae may be used as a carotenoid-containing mixture. One example of algae that is grown specifically for its high concentration of certain carotenoids is *Haematococcus pluvialis*. Exemplary plant or vegetable substrates that contain various carotenoids are tomato, corn, marigold and spinach.

Typically, the carotenoid-containing mixture is charged to the extraction vessel as a dehydrated solid powder of algae or vegetable substrate. The bulk density of these powders can range from about 0.2 g/cc to 0.8 g/cc. One having ordinary skill in the art will understand, however, that the present invention is in no way limited to solid feeds or to solid feeds of this range of bulk density, since liquid carotenoid-containing extracts can also be used. The amount of substrate used in any test or production run is related to the volume of the extraction vessel. For instance, if a 1-liter extraction vessel is used to extract a solid feed with a bulk density of 0.5 g/cc, then approximately 500 grams of substrate will be charged to the vessel.

In one embodiment, only supercritical or liquefied dimethyl ether is used to extract essentially all of the extractable lipids and carotenoids thereby producing a total extract. In another embodiment a liquefied or supercritical gas such as carbon dioxide is first used to extract lipids from the substrate. The lipids obtained through this step are essentially free of carotenoids.

Specific conditions of pressure and temperature used to process any particular material are chosen based upon the specific nature of the substrate and the compound to be solubilized and extracted. For example, the temperature of the solvent can be in the range of about −5° C. to 140° C. while the pressure of the solvent can be in the range of about 100 psi to 5000 psi. Dimethyl ether, at a temperature of 25° C. and 200 psi, can extract essentially all the carotenoids from a substrate. Solubility will determine the amount of supercritical or liquefied solvent that should be used, that is, the solvent-to-feed ratio.

Figure 2:
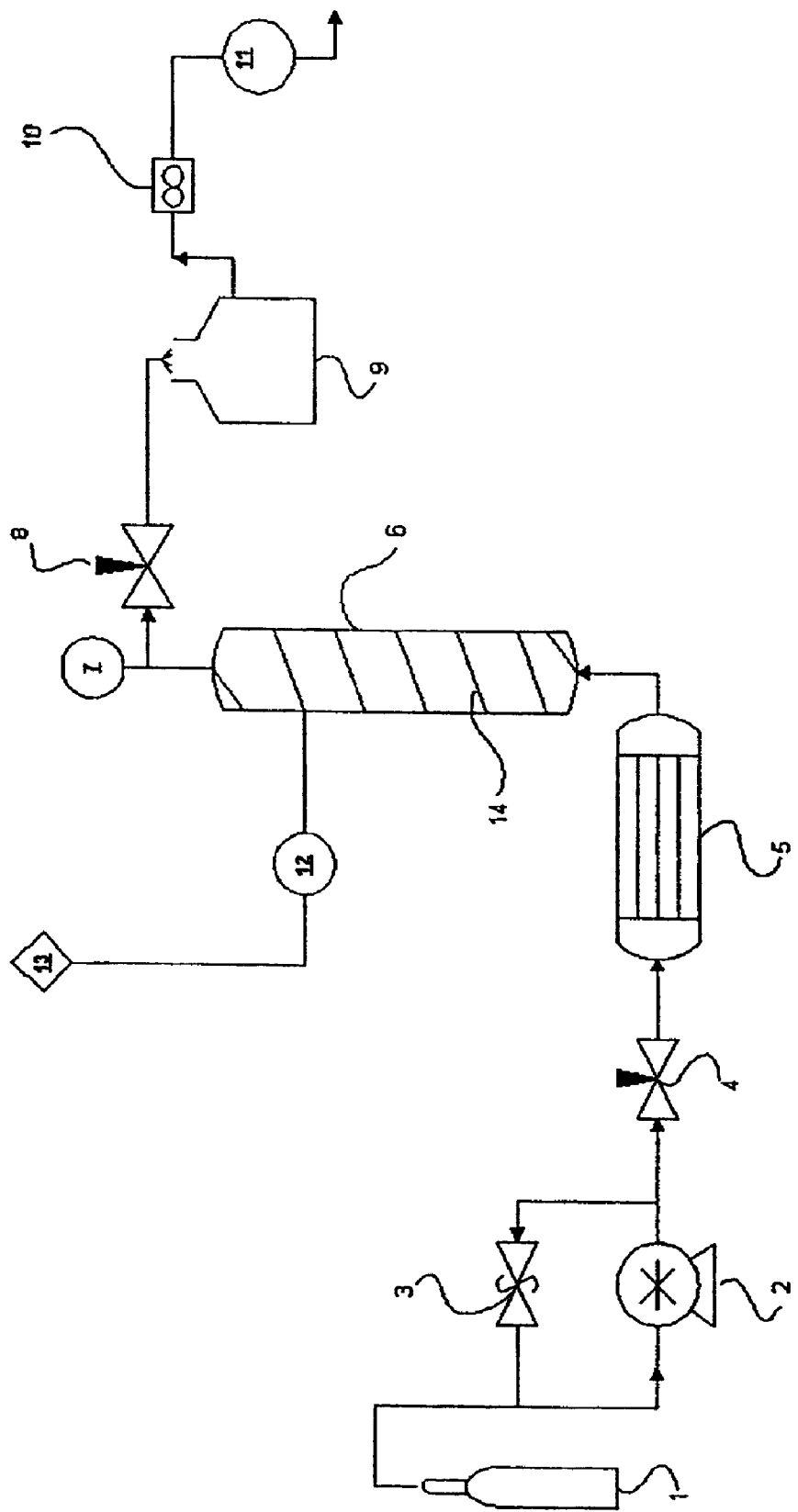
FIG. 2 is a schematic diagram of an extraction system for use with the present invention.

FIG. 2 is a schematic diagram of an exemplary embodiment of a laboratory flow apparatus that may be used specifically for fractionation/extraction of carotenoids. During a typical extraction, a substrate from which carotenoid is to be extracted is charged to extraction vessel 6 and the vessel is sealed. Liquefied, gas is compressed from supply cylinder 1 by diaphragm compressor 2 (Newport Scientific) to a desired pressure, which can be controlled by back pressure regulator 3 (Tescom Corporation). Compressed gas is metered through needle valve 4 or a similar valving arrangement known in the art. Compressed gas is delivered at a flow rate from about 20 g/min to 200 g/min to a surge tank/pre-heater 5 that is in series with the extraction vessel 6. Pressure is controlled to within ±5 bar and the flow rate is controlled by pressure-reduction valve 8. The temperature of the extraction vessel 6 is maintained to within 2° C. as measured by thermocouple 7 located at the exit of the extraction column 6; another thermocouple 12 shown located on the outside skin of the extraction chamber 6 senses the temperature of the extraction chamber, which can be controlled by electrical heating tape 14 that is regulated by an PID controller 13 (Omega Engineering). Downstream of extractor 6, the solvent, laden with dissolved material extracted from the charge, is expanded to atmospheric pressure via the pressure reduction valve 8 causing the extracted material to precipitate. The extracted precipitate is collected in a pre-weighed collection flask 9. A filter can be placed in the exit of the flask 9 to trap any fine particles entrained in the gas. The ambient gas passes through a flow meter 10 (Fischer-Porter) and a dry test meter (DTM) 11 (Singer) to measure, respectively, the instantaneous flow rate and the total volume passed through the extractor. All process tubing, vessels, and valves are preferably constructed of 304 or 316 stainless steel.

Procedure for Extraction of Astaxanthin

As to the methodology for extraction of astaxanthin from algae, a known quantity of *Haematococcus pluvialis* is charged to the extraction chamber 6 and the chamber sealed and brought to process temperature and pressure. The gas (either in supercritical fluid or liquefied state) is passed through the extractor 6. The gas and dissolved extract exits the vessel 6 through the pressure-reduction valve 8. The material that was dissolved in the supercritical fluid, depending upon extraction conditions and gas used precipitates in the collection chamber 9 and the now ambient gas exits the collector 9 and is measured in volume by DTM 11.

Several examples give the results of operation under the embodiments described.

EXAMPLE 1

Following the procedure described above, 31.0 grams of *Haematococcus pluvialis* algae was charged to the extraction vessel and dimethyl ether was used as the extracting solvent. Dimethyl ether was used in its liquefied state at 1500 psi and 45° C. A quantity of 900 grams of dimethyl ether was passed through the extraction vessel, and 8.9 grams of extract was collected. The spent biomass was then recovered from the vessel and the extract and the biomass were analyzed for astaxanthin content. Table 1 shows the analytical results.

TABLE 1

ANALYTICAL RESULTS FOR EXAMPLE 1

| Sample | Weight (grams) | Concentration of Astaxanthin (% w/w) |
|---|---|---|
| Charge of algae | 31.0 | 1.6 |
| Extract | 8.9 | 5.5 |
| Residue | 21.7 | 0.08 |

Substantially, all of the astaxanthin from the charge of algae was recovered in the extract; the yield was 98%.

EXAMPLE 2

A quantity (46.1 grams) of *Haematococcus pluvialis* was charged to the extraction vessel. A two step procedure was employed in order to concentrate the recovered astaxanthin to a greater degree. In the first step, supercritical carbon dioxide at 60° C. and 2800 psi was used, and a total of 1200 grams of gas was passed through the extraction vessel. A total of 8.1 grams was extracted in this first fraction. The experimental system was then degassed to atmospheric pressure. A total of 500 g of liquified dimethyl ether at 40° C. and 1500 psi was then passed through the extraction chamber and 5.1 grams of viscous liquid was extracted. Thus, a total of 13.2 grams of extract was collected in the two fractions. A yield of 31.6 grams of biomass was recovered as residue from the extraction chamber. The weights and astaxanthin concentration are summarized in Table 2.

TABLE 2

ANALYTICAL RESULTS FOR EXAMPLE 2

| Sample | Weight (grams) | Concentration of Astaxanthin (% w/w) |
|---|---|---|
| Charge of algae | 46.1 | 1.6 |
| $CO_2$ fraction | 8.1 | 0.05 |
| Dimethyl Ether fraction | 5.1 | 14.2 |
| Residue | 31.6 | 0.10 |

As Table 2 shows, the content of astaxanthin in the concentrated fraction was 14.2% and the yield was 98%.

EXAMPLE 3

A third example demonstrates an alternative two step process. In the first step, the astaxanthin and associated lipid in the algae substrate was extracted with dimethyl ether following the procedure of Example 1. Then, in a counter current column, a second step involving stripping off the lipid portion of the resulting extract with sub or supercritical carbon dioxide was carried out. For this example, 56.3 grams of *Haematococcus pluvialis* algae was loaded to the extraction vessel and 900 grams of dimethyl ether at 1500 psi and 45° C. was passed through the bed of algae. A total of 15.8 grams of extract was obtained. This extract was then charged to another extraction vessel to simulate a counter-current column and supercritical carbon dioxide was passed through the new charge (of 15.8 g) at 2800 psi and 40° C. In this step 9.7 grams of a low viscosity, oily material was extracted with supercritical $CO_2$, and a quantity of 6.0 grams of remaining material was drained from the extractor as a raffinate. The material balance and analytical results for this third example are given in Table 3.

TABLE 3

ANALYTICAL RESULTS FOR EXAMPLE 3

| Sample | Weight (grams) | Concentration of Astaxanthin (% w/w) |
|---|---|---|
| Charge of algae | 56.3 | 1.6 |
| First extract (dimethyl ether) | 15.8 | 5.6 |
| Second extract ($CO_2$) | 9.7 | 0.1 |
| Raffinate | 6.1 | 14.5 |

A high concentration of astaxanthin was again achieved in the concentrate fraction and the yield was 97%. This example demonstrates the concentration of astaxanthin that can be achieved in a countercurrent extraction process to separate the lipid from the lipid-astaxanthin extract that has been previously extracted from algae using dimethyl ether.

Similar results have been obtained using dimethyl ether extraction and/or the two step processes described herein of tomato pulp and skins for lycopene, marigold petals for lutein, red peppers for β-carotene, corn for lutein and zeaxanthin, and spinach for lutein.

EXAMPLE 4

As shown below, supercritical fluids are effective for removing residual liquid organic solvents from astaxanthin extracted from a substrate by the liquid organic solvents. Supercritical fluids under other conditions can also remove solvents and lipids from the astaxanthin extract to produce a solvent-free concentrated astaxanthin product.

A quantity of 68.4 g of *Haematococcus pluvialis* was charged to a 1 L beaker. A quantity of 300 ml acetone was added to extract lipids and astaxanthin from the algae. The suspension was stirred for 60 minutes, then the contents of the beaker poured into a Buchner funnel filter. The cake from this filtration was placed in the 1 L beaker with 130 ml additional acetone, stirred for 60 minutes, and the suspension filtered.

The filter cake was oven dried. The two filtrates were combined, and the acetone was evaporated under vacuum for a series of 24 hrs. The dried filter cake (the Residual) weighed 48.2 g. After evaporation of the acetone the lipid and astaxanthin extract weighed 20.3 g. The extract was charged to the high pressure extraction vessel, and 400 g of supercritical carbon dioxide at 40° C. and 1200 psi was passed through the charge. A quantity of 0.5 g of clear, pale red liquid was collected in the trap. It was not analyzed, but it exhibited the characteristic odor of acetone, and the clear pale red color indicated only scant astaxanthin was in the acetone. The pressure in the vessel was then increased to 2800 psi, and a quantity of 1000 g of carbon dioxide was passed through the charge. A low viscosity dark red liquid weighing 6.3 g was collected. Thereafter, 12.5 g of high viscosity very dark red liquid was removed from the vessel.

Table 4 illustrates the analytical results obtained from the samples of Example 4.

TABLE 4

ANALYTICAL RESULTS FOR EXAMPLE 4

| Sample | Weight (grams) | Concentration of Astaxanthin (% w/w) |
|---|---|---|
| Charge of algae | 68.4 | 1.6 |
| Extract (after evaporation of Acetone) | 20.3 | 5.4 |
| Extract remaining after removal of Acetone by $CO_2$ at 1100 psi | 19.8 | 5.4 |
| Extract remaining after removal of lipids by $CO_2$ at 2800 psi | 12.5 | 8.3 |
| Residual (dried filter cake) | 48.2 | 0.12 |

The analytical results and the weights measured from the extraction described in Example 4 show that residual organic solvent can be removed from a solvent-containing extract of algae, and that the astaxanthin can further be concentrated using supercritical carbon dioxide to remove essentially only lipids from the extract that was obtained by an extraction using acetone (or other organic liquid).

One of ordinary skill in the art will appreciate further features and advantages of the invention based on the above-described embodiments. Accordingly, the invention is not to be limited by what has been particularly shown and described as examples. All references cited herein are expressly incorporated by reference in their entirety.

What is claimed is:

1. A method for deriving a carotenoid material, comprising:
    providing a mixture comprising carotenoid material;
    contacting the mixture with a supercritical fluid capable of selectively extracting the mixture substantially without extracting the carotenoid material, to obtain an extract of predominantly lipid composition and a partially extracted portion of the mixture that is enriched in carotenoids; and
    contacting the partially extracted portion with dimethyl ether to extract the carotenoid material to derive a carotenoid material.

2. The method of claim 1 wherein the supercritical fluid is carbon dioxide.

3. The method of claim 1 wherein the mixture comprises an algae-derived material.

4. The method of claim 1 wherein the mixture comprises material derived from a marine organism.

5. The method of claim 1 wherein the mixture comprises material derived from a vegetable.

6. A method for deriving enriched carotenoid material, comprising:
    providing a mixture comprising carotenoid material;
    extracting the mixture with dimethyl ether forming an extracted portion comprising a mixture of carotenoid material and lipids; and
    contacting the extracted portion with a supercritical fluid to perform at least one of:
        i) selectively extracting the carotenoid material from the extracted portion; and
        ii) selectively separating a fraction of the extracted portion substantially without extracting any carotenoid material; and
    collecting a concentrated carotenoid fraction as a raffinate.

7. A method for deriving enriched carotenoid material, comprising:
    providing a mixture comprising organic solvent extracted carotenoid material; and
    extracting the mixture with carbon dioxide to obtain a solvent or a solvent and lipid portion and concentrated carotenoid portion free of organic solvent.

* * * * *